United States Patent [19]

Speranza et al.

[11] Patent Number: 5,001,267

[45] Date of Patent: Mar. 19, 1991

[54] SECONDARY ALKYL AMINE DERIVATIVES OF ETHYLENEDIAMINE

[75] Inventors: George P. Speranza, Austin; Jiang-Jen Lin, Houston; James H. Templeton; Wei-Yang Su, both of Austin, all of Tex.

[73] Assignee: Texaco Chemical Company, White Plains, N.Y.

[21] Appl. No.: 322,021

[22] Filed: Mar. 13, 1989

Related U.S. Application Data

[63] Continuation-in-part of Ser. No. 135,798, Dec. 21, 1987, abandoned.

[51] Int. Cl.$^5$ .............................................. C07C 209/26
[52] U.S. Cl. ..................................... 564/472; 540/575
[58] Field of Search ......................... 564/472; 540/575

[56] References Cited

U.S. PATENT DOCUMENTS

| | | | |
|---|---|---|---|
| 3,117,999 | 1/1964 | Boettner et al. | 260/54 |
| 3,192,113 | 6/1965 | Thomas | 167/65 |
| 3,364,239 | 1/1968 | Speranza | 260/347.7 |
| 4,417,075 | 11/1983 | Stogryn | 564/505 |
| 4,429,157 | 1/1984 | Disteldorf et al. | 564/446 |
| 4,471,138 | 9/1984 | Stogryn | 564/508 |
| 4,806,690 | 2/1989 | Bowman | 564/480 |

FOREIGN PATENT DOCUMENTS 1396985  6/1975  United Kingdom .

*Primary Examiner*—Glennon H. Hollrah
*Assistant Examiner*—P. O'Sullivan
*Attorney, Agent, or Firm*—Jack H. Park; Kenneth R. Priem; Carl G. Ries

[57] ABSTRACT

Secondary alkyl amine derivatives of ethylenediamine are formed in a one-step reaction when ethylenediamine is substantially simultaneously continuously mixed with a methyl alkyl ketone to form a reaction mixture which is continuously hydrogenated in the presence of a hydrogenation catalyst and hydrogen, the alkyl group containing 1 to 4 carbon atoms.

4 Claims, No Drawings

SECONDARY ALKYL AMINE DERIVATIVES OF ETHYLENEDIAMINE

RELATED APPLICATION

This application is a continuation-in-part of copending Speranza et al. U.S. pat. application Ser. No. 07/135,798, filed Dec. 21, 1987, and entitled "Secondary Isopropyl Amine Derivatives of Polyoxyalkylene Diamines and Triamines" now abandoned.

BACKGROUND OF THE INVENTION

1. Technical Field of the Invention

This invention relates to secondary alkyl amine derivatives of ethylenediamine. More particularly, this invention relates to secondary alkyl amine derivatives of ethylenediamine prepared by the reaction of ethylenediamine with a methyl alkyl ketone in the presence of hydrogen and a hydrogenation catalyst. Still more particularly, this invention relates to a continuous method utilizing a methyl alkyl ketone wherein the alkyl group contains 1 to 4 carbon atoms wherein ethylenediamine is continuously reacted with the methyl alkyl ketone in the presence of hydrogen and a hydrogenation catalyst to provide secondary alkyl amine derivatives of ethylenediamine.

2. Prior Art

Speranza et al. U.S. Pat. No. 3,110,732 is directed to a method for preparing primary amine derivatives of polyoxyalkylene glycol by a three-step process wherein an alkanolamine having a primary amine group is reacted with a higher carbonyl compound such as methylethyl ketone, isobutyraldehyde, etc., to form a condensation product which may be either a Schiff base or an oxazolidine which is thereafter alkoxylated with an alkylene oxide to provide an adduct followed by hydrolysis of the adduct to form a primary amine basic polyether composition.

Speranza U.S. Pat. No. 3,364,239 is directed to secondary amino polyalkoxy monoalkanols which are prepared by reacting a primary amino polyalkoxy alkanol with a higher carbonyl compound such as methylethyl ketone, butyraldehyde, etc., to form a Schiff base reaction product which is thereafter hydrogenated in the presence of a hydrogenation catalyst at an elevated temperature and pressure to provide the secondary amino polyalkoxy monoalkanol. The reference contains an example III wherein acetone was reacted in an autoclave with aminoethoxyethanol in the presence of hydrogen and a hydrogenation catalyst to provide a reaction product comprising N-isopropylaminoethoxyethanol.

Malz, Jr. et al. U.S. Pat. No. 4,607,104 is directed to a process wherein 2,2,6,6-tetraalkyl-4-piperidylamines are prepared by reacting an amine with 2,2,6,6-tetraalkyl-4-piperidone in the presence of water, an aliphatic alcohol or aliphatic glycol and a platinum, nickel or cobalt catalyst.

BACKGROUND OF THE PRESENT INVENTION

As exemplified by the Speranza and Speranza et al. patents, it is known that when a higher ketone such as methylethyl ketone is reacted with a primary amine the reaction product is a Schiff base or an oxazolidine. This Schiff base may thereafter be hydrogenated to provide a secondary amino polyalkoxy alkanol. Thus, a two-step reaction is required. Moreover, acetone is not a suitable ketone for the use in a two-step reaction of this nature because of its boiling point.

Parent Speranza et al. U.S. patent application Ser. No. 07/135,798 filed Dec. 21, 1987 and entitled "Secondary Isopropyl Amine Derivatives of Polyoxyalkylene Diamines and Triamines" is directed to secondary isopropyl amine derivatives of polyoxyethylene and/or polyoxypropylene primary diamines or triamines prepared by reacting the polyoxyethylene diamine or triamine or the polyoxypropylene diamine or triamine with acetone in the presence of hydrogen and a hydrogenation catalyst.

In parent copending Speranza et al. U.S. patent application Ser. No. 07/135,798, on page 24 thereof, and in respect of experimental batch runs that are there discussed, it is stated that an attempt to react acetone with ethylenediamine in the presence of hydrogen and a hydrogenation catalyst at a 3:1 mol ratio was unsuccessful (i.e., there was no detectable formation of either N,N'-diisopropyl ethylenediamine or N'-isopropyl ethylenediamine). However, on page 27 of the application, in reporting on experimental results obtained using a continuous reactor, it was reported that at a molar ratio of ethylenediamine to acetone of 3:1 there was about a 100% conversion of the ethylenediamine with a selectivity to N,N'-diisopropyl ethylenediamine of about 70% and a selectivity to N'-isopropyl ethylenediamine of about 20%.

It has now been discovered, in accordance with the present invention, that these anomalous results, as reported in parent Speranza et al. U.S. application Ser. No. 07/135,798, result from the propensity of ethylenediamine to react with acetone at room temperature to form a heterocyclic compound having the formula:

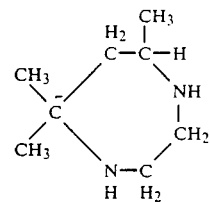

It has further been discovered, in accordance with the present invention, and as reported and shown in copending parent Speranza et al. U.S. patent application Ser. No. 07/135,798, on pages 27 and 28 that this problem can be overcome when ethylenediamine and acetone are continuously reacted in the presence of hydrogen and a hydrogenation catalyst under appropriate reaction conditions, provided that the ethylenediamine and acetone are not mixed with each other until just before the resultant mixture is charged to a continuous reactor. That is to say, the configuration of the reactor and the reaction conditions employed should be such that the holding time of the mixture of ethylenediamine with acetone prior to reaction, as specified herein, is kept to a minimum.

It is still further reported in parent Speranza et al. U.S. patent application Ser. No. 07/135,798 on pages 2 and 3 that higher ketones normally react with primary amines to form a Schiff base or an oxazolidine. The Schiff base or oxazolidine can be hydrogenated to provide a secondary amino polyalkoxy alkanol, but as a consequence, a two-step reaction is required.

We have still further discovered, in accordance with the present invention, that ethylenediamine can also be reacted with methyl alkyl ketones homologous to acetone under the continuous reaction conditions of the present invention to provide additional secondary alkyl amine derivatives of ethylenediamine.

SUMMARY OF THE PRESENT INVENTION

The starting materials for the present invention are ethylenediamine, hydrogen, a hydrogenation catalyst and a methyl alkyl ketone having the formula:

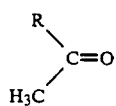

wherein R represents an alkyl group having one to four carbon atoms.

Examples of suitable methyl alkyl ketones that may be used in the practice of the present invention include acetone, methyl ethyl ketone, methyl n-propyl ketone, methyl isopropyl ketone, methyl n-butyl ketone, methyl isobutyl ketone, etc.

It is important that the ketone be used in the correct proportions if the desired products are to be obtained with good yield and selectivity. Suitably, the ratio of methyl alkyl ketone to ethylenediamine will be in the range of about 1:1 to about 4:1 and, more preferably, in the range of about 1.2:1 to about 3:1.

Hydrogen

The methyl alkyl ketone is reacted with the ethylene diamine in the presence of added hydrogen. The reaction is conducted at an elevated temperature and pressure. Normally, the reactants can be pressured at a desired pressure with hydrogen and hydrogen may be used thereafter to maintain the pressure so that the reaction pressure and the hydrogen partial pressure will be essentially the same. The reaction pressure should be within the range of about 500 to about 5000 psi., including a hydrogen partial pressure of about 50 to about 2,500 psi., and more preferably a pressure of about 1000 to 4000 psi., such that at least about a 50% molar excess of hydrogen is present.

The Hydrogenation Catalyst

Any suitable pelleted hydrogenation catalyst may be used such as a catalyst comprising one or more of the metals of group VIIIB of the Periodic Table, such as iron, cobalt, nickel, ruthenium, rhodium, palladium, platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 to 85 mole percent of nickel, about 14 to 37 mole percent of copper and about 1 to about 5 mole percent of chromium (as chromia), such as a catalyst disclosed in Moss U.S. Pat. No. 3,151,112 or Yeaky U.S. Pat. No. 3,654,370. As another example, a catalyst of the type disclosed in Boettger et al. U.S. Pat. No. 4,014,933 may be used containing from about 70 to about 95 wt. % of a mixture of cobalt and nickel and from about 5 to about 30 wt. % of iron. As another example, a catalyst of the type disclosed in Habermann U.S. Pat. No. 4,152,353 may be used, such as a catalyst comprising nickel, copper and a third component which may be iron, zinc, zirconium or a mixture thereof, e.g., a catalyst containing from about 20 to about 49 wt. % of nickel, about 36 to about 79 wt. % of copper and about 1 to about 15 wt. % of iron, zinc, zirconium or a mixture thereof.

Reaction Conditions

The reaction should be conducted continuously at a temperature within the range of about 100° to about 300° C., and more preferably at a temperature within the range of about 120° to about 200° C. and at a pressure within the range of about 1000 to about 4000 psig, and more preferably at a pressure within the range of about 2,000 to about 4,000 psig, including a hydrogen partial pressure of about 50 to about 2500 psi, such that there is at least a 50% molar excess of hydrogen in the reactor, based on the acetone.

The reaction should be conducted on a continuous basis, preferably in a reactor containing a bed of a pelleted hydrogenation catalyst and the ethylenediamine and the methyl alkyl ketone should not be mixed until just prior to the time when they are charged to the reactor. The feed rate for the mixture of ethylenediamine and methyl alkyl ketone should be within the range of about 0.5 to about 3 w/hr/v.

When the feedstocks are acetone and ethylenediamine and it is desired to maximize the production of N-isopropyl ethylenediamine, the continuous reaction conditions should include a temperature within the range of about 130° to about 180° C., a pressure within the range of about 1000 to about 4000 psig, and a feed rate for the combined mixture of acetone and ethylenediamine of about 1 to about 3 w/hr/v when using a preferred nickel, copper, chromia catalyst containing about 60 to about 95 mole percent of nickel, about 14 to about 37 mole percent of copper and about 1 to about 5 mole percent of chromium, as chromia.

Structure

The secondary alkyl amine derivatives of ethylenediamine include the mono N-alkyl derivate and the N,N'-dialkyl derivative, as follows:

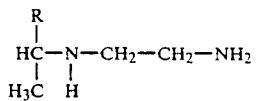

and

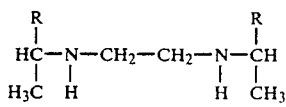

wherein R represents an alkyl group containing 1 to 4 carbon atoms.

UTILITY

The products prepared by the present invention are useful for a number of purposes. For example, they may be used as curing agents for epoxy resins. They may be used to prepare aminoalkylacrylamide monomers and may also be used to prepare intermediates useful in the pharmaceutical industry.

WORKING EXAMPLES

Continuous runs were carried out in a 500 cc and a 600 cc stainless steel tubular, upward flow reactors heated with an aromatic hydrocarbon heat transfer agent. The reactors had an inside diameter of 1.338 inches and various lengths of catalyst beds varying from about 20 to about 60 inches. A thermowell fabricated from ¼-inch o.d. tubing extended upward into the catalyst bed to allow temperature measurements at four different points. The catalysts beds were filled with a pelleted catalyst composed of a nickel, copper, chromia catalyst containing about 75 mole % of nickel, about 23 mole % of copper and about 2 mole % of chromium.

was carried out at about 100° C., about 125° C., and about 150° C. in individual runs. The results are given in Table II.

TABLE I

Preparation of Mono & Diisopropyl Ethylenediamine - Feeds Ratio Profile[a]

| Notebook No. | Moles Acetone:EDA | Reaction Temp., °C. | % Water + Isopropanol | % EDA | % Mono | % Di | Mono Di | % Higher Boilers | Space Velocity |
|---|---|---|---|---|---|---|---|---|---|
| 6380-56 | 1.25:1 | 150 | 30.0 | 16.6 | 42.5 | 7.3 | 5.82 | 4.0 | 2 |
| 6380-53 | 1.50:1 | 150 | 32.6 | 11.1 | 52.1 | 10.3 | 4.09 | 4.0 | 2 |
| 6380-87 | 1.75:1 | 150 | 42.0 | 7.0 | 35.7 | 10.0 | 3.57 | 4.0 | 2 |
| 6380-54 | 1.26:1 | 150 | 33.0 | 15.3 | 41.1 | 7.0 | 5.87 | 3.6 | 1 |

[a]2500 psig, 100% excess of $H_2$

TABLE II

Preparation of Mono % Diisopropyl Ethylenediamine - Temperature Profile[a]

| Notebook No. | Moles Acetone:EDA | Reaction Temp., °C. | % Water + Isopropanol | % EDA | % Mono | % Di | Mono Di | % Higher Boilers | Space Velocity |
|---|---|---|---|---|---|---|---|---|---|
| 6380-50-1 | 1.5:1 | 100 | 28.0 | 18.0 | 4.3 | 2.5 | — | 48.0 | 1 |
| 6380-50-2 | 1.5:1 | 125 | 28.5 | 8.5 | 38.8 | 9.0 | 4.3 | 9.9 | 1 |
| 6380-50-3 | 1.5:1 | 150 | 30.9 | 8.5 | 44.0 | 12.0 | 3.7 | 4.5 | 1 |

[a]2500 psig, 100% excess of $H_2$

Reaction of Ethylenediamine (EDA) with Acetone

In an initial group of experiments, we examined the reaction of EDA with acetone at various feed ratios. Acetone and EDA were pumped separately and were combined into a single liquid feed before entering the bottom of the reactor. The total space velocity of acetone plus EDA was kept at the same level, 2 g/cc-catalyst/hr. Hydrogen was charged to the bottom of the reactor in 100% excess (based on the amount of acetone charged). The reaction temperature was maintained at 150° C., "hot spot" temperature. Reactor effluent was cooled and passed through a back-pressure regulator set to maintain 2500 psig. pressure on the reactor. Effluent from this regulator was discharged into a receiver in which liquid product was collected at atmospheric pressure and from which gases were vented. The products were analyzed by GLC. The area percent composition for all components of the crude effluent sample were determined for each run. Three runs were conducted at acetone/EDA mole ratios of 1.25, 1.5 and 1.75 and the results are given in Table I. Not surprisingly, the selectivity of the reaction toward monoisopropyl EDA and diisopropyl EDA depends on the ratio of acetone/EDA. Lowering the acetone/EDA ratio results in higher selectivity of monoisopropyl EDA. For instance, with an acetone/EDA mole ratio of 1.75, the reaction mixture contained about 35.7% of monoisopropyl EDA, about 10% of diisopropyl EDA and about 7% of unreacted EDA. When the acetone/EDA mole ratio was decreased to 1.25, the amount of monoisopropyl EDA was increased to 42.5% and the amount of diisopropyl EDA was decreased to 7.3%. Moreover, EDA conversion declined at the lower ratio.

In order to obtain more information, the reaction profile as a function of temperature was conducted at 2500 psig. and a total space velocity of 1 g/cc-catalyst/hr, and an acetone/EDA mole ratio of 1.5, in the presence of 100% excess of hydrogen. The reaction These results show that a high production rate of substituted EDA is obtained at the higher reaction temperature, i.e., 150° C. At 100° C., there was a loss of selectivity with by-product formation. Thus, at 100° C., the reaction product contained both N-isopropyl-N'-isopropylidine EDA and, predominantly N,N'-bisisopropylidine EDA. The reaction tends to favor the formation of disubstituted EDA because lesser amounts of acetone are reduced.

Next, we sought to gain additional insight into the mechanism of the reaction and to obtain higher yields of N-isopropyl EDA by examining the reaction of EDA with acetone under different conditions—especially at higher temperatures. Reactions were conducted at acetone/EDA mole ratios of 2 and 1.25 and at 150° C., 175° C., and 200° C., respectively. The results are listed in Table III. These results again demonstrate that at higher temperatures or higher acetone/EDA ratios, the reaction of EDA with acetone gives higher EDA conversion and a higher diisopropyl EDA selectivity. Increasing the reaction temperature drastically lowers the selectivity of the monoisopropyl EDA product. For example, when the reaction temperature was increased from 150° to 200° at an acetone/EDA mole ratio of 2, the weight ratio of mono/diisopropyl derivative was decreased from 1.74 to 0.14. When the reaction temperature was increased from 150° to 200° C. and at an acetone/EDA mole ratio of 1.25, the weight ratio of mono/diisopropyl derivative was decreased from 5.8 to 2.14. It thus appears from the data that at higher temperatures, acetone reacts with amines to a much greater extent than it does at lower temperatures and that the rate of acetone reduction is not increased as much as the rate of by-product formation. However, with lower acetone/EDA ratios (i.e., 1.25) and at a higher temperature (i.e., 175° C. or more), several percentages of piperazine by-product were formed in the reaction. This is particularly disadvantageous because N-isopropyl EDA and piperazine form an azeotrope. Moreover, at the higher temperatures, it appears that there was some production of polyethylenepolyamine derivatives.

We found that no significant change in product distribution occurred while changing the space velocity of the reaction to 150° C. (compare run 6380-56 with run 6380-54 of Table I). Therefore, at higher temperatures, by increasing the space velocity, the amines have less time to be coupled to give by-products and the relative rate of reductive amination does not slow down since the reaction temperature is sufficiently high. In addition, by using about 50% or more of excess hydrogen, such as 100% excess, no effect on the product distribution was determined.

-continued

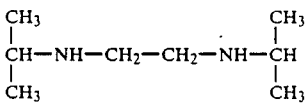

TABLE III

| | Preparation of Mono % Diisopropyl Ethylenediamine - Higher Temperature[a] | | | | | | | | |
|---|---|---|---|---|---|---|---|---|---|
| Notebook No. | Moles Acetone:EDA | Reaction Temp., °C. | % Water + Isopropanol | % EDA | % Mono | % Di | Mono Di | % Higher Boilers | Space Velocity |
| 6380-67-1 | 2:1 | 150 | 36.1 | 2.2 | 35.2 | 20.2 | 1.74 | 5.3 | 2 |
| 6380-67-2 | 2:1 | 175 | 32.3 | — | 24.0 | 32.0 | 0.75 | 11.7 | 2 |
| 6380-67-3 | 2:1 | 200 | 29.4 | 0.4 | 5.4 | 38.2 | 0.14 | 25.2 | 2 |
| 6380-56[b] | 1.25:1 | 150 | 30.0 | 16.6 | 42.5 | 7.3 | 5.82 | 4.0 | 2 |
| 6380-72-1 | 1.25:1 | 175 | 25.2 | 7.9 | 48.8 | 10.4 | 4.69 | 7.0 | 2 |
| 6380-72-2 | 1.25:1 | 200 | 28.4 | 0.4 | 27.6 | 12.9 | 2.14 | 26.6 | 2 |
| 6380-76 | 1.25:1 | 200 | 20.8 | — | 37.6 | 14.2 | 2.65 | 22.5 | 3 |

[a]2500 psig, 50% excess of $H_2$
[b]100% excess of $H_2$

We also found that if the mixture of ethylenediamine with acetone was permitted to stand at room temperature, a heterocyclic product is formed which is not reductively hydrogenated in the reactor to the desired products.

It appears from the experimental results that the reaction of the ethylenediamine with acetone may proceed in the following manner.

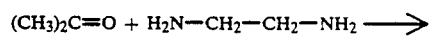

(I)

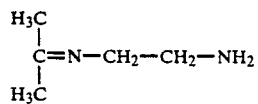

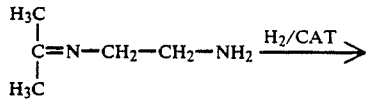

(II)

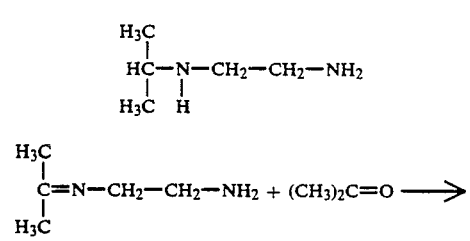

(III)

(IV)

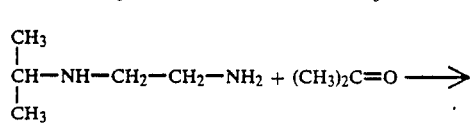

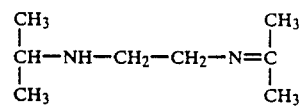

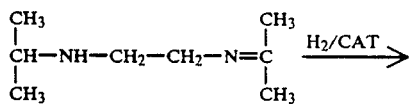

(V)

Distillation of the reaction products formed by the continuous reactions into fractions indicate that N-isopropyl ethylenediamine can be recovered from the reaction product with a purity of 99% or more. This fraction boiled at a temperature of about 137°–139° C. A fraction obtained at a temperature of 167°–169° C. consisted essentially of N,N'-diisopropyl ethylenediamine.

It was further found, however, that ethylenediamine, N-isopropyl ethylenediamine and N,N'-di-isopropyl-ethylene-diamine form a ternary azeotrope that boiled at about 114° to about 125° C. Therefore, it is important to obtain both a high degree of conversion of the ethylenediamine and a high selectivity to N-isopropyl ethylenediamine to minimize the formation of the ternary azeotrope.

Reaction of Ethylenediamine with Other Methyl Alkyl Ketones

Additional continuous runs were carried out to study the reaction of ethylenediamine with other methyl alkyl ketones, as illustrated by the following equation:

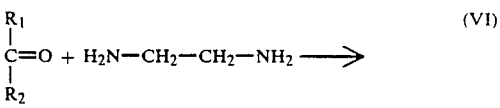

(VI)

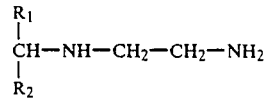

and

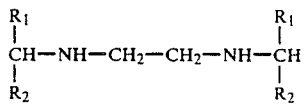

wherein $R_1$ represents a methyl group and $R_2$ represents an alkyl group containing 1 to 4 carbon atoms.

In conducting each run, ethylenediamine and the methyl alkyl ketone reactant were pumped separately at desired rates and mixed into a single liquid feed before entering the bottom of the reactor. Hydrogen was also charged to the bottom of the reactor. Feed rates were adjusted to a feed mole ratio of 1.2 moles of methyl alkyl ketone per mole of EDA at a space velocity of 1 gram of liquid feed per hour per milliliter of catalyst using a 100% excess of hydrogen, basis the methyl alkyl ketone charge. The liquid and gas feeds were passed upwardly through the catalyst bed which was maintained at a temperature of about 150° C. Reactor effluent was cooled and passed through a back pressure regulator set to maintain 2500 psig. pressure on the reactor. Effluent was discharged into a receiver in which liquid product was collected at atmospheric pressure and from which gases were vented. The products were analyzed by GLC. The area percent compositions for all components in the crude effluent samples were determined using an OV-17 column and a thermal conductivity detector. The methyl alkyl ketones tested and the results obtained are listed in Table IV. The results show that for the less hindered methyl alkyl ketones, the mono alkyl ethylenediamine is the preferred product. However, with methyl isobutyl ketone, a hindered ketone, the reaction produced a significantly larger percentage of the dialkyl ethylenediamine. It is postulated that the rate of mono alkylated monoalkylation is relatively slow due to the low solubility of the mono alkylated monoalkylation product in the ketone and ethylenediamine and that the second reductive amination is the more critical reaction due to the increasing solubility of the monosubstituted amine in the ketone.

The products of each run were distilled through a two foot vacuum jacketed fractional distillation column. The boiling points of N-3'-pentylethylenediamine, N-2'-butyl-ethylenediamine and N-4'-methyl-2'-pentaethylenediamine were found to be 178° C., 160° C., and 188° C., respectively.

TABLE IV

| | | Preparation of Mono & Dialkyl Ethylenediamine[a] | | | | | | |
|---|---|---|---|---|---|---|---|---|
| Notebook No. | Mole Ratio of Ketone:EDA | Temp (°C.) | Alkanol + Water % | EDA (%) | Mono (%) | Di (%) | % Higher Boilers | Space Velocity |
| 6380-82 | 1.2[b]:1 | 150 | (63.8) | (13.4) | 19.9 | 0.8 | 2.1 | 1 |
| 6380-16 | 1.2[c]:1 | 150 | 47.9 | 16.8 | 31.1 | 4.2 | — | 1 |
| 6380-19 | 1.2[d]:1 | 150 | 48.1 | 15.5 | 18.3 | 13.4 | 2.8 | 1 |

[a]2500 psig, 100% excess H$_2$
[b]Diethyl Ketone
[c]Methyl Ethyl Ketone
[d]Methyl Isobutyl Ketone With reference to Table IV it is to be noted that when the feed was diethyl ketone unsatisfactory results were obtained in that only a small amount of the N-diethyl derivative of ethylenediamine was formed and in that there was a very significant formation of lighter by-products.

The foregoing examples have been given by way of illustration only and are not intended as limitations on the scope of this invention, as defined by the appended claims.

What is claimed is:

1. A method for the continuous production of a N-isopropyl amine derivative of ethylenediamine by the reaction of acetone with ethylenediamine wherein the formation of an addition product of acetone with ethylenediamine is substantially completely inhibited, said addition product having the formula:

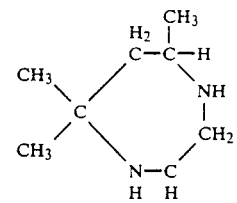

said method comprising the steps of:
a. substantially simultaneously continuously mixing ethylenediamine with acetone in the molar ratio of about 2.1 to about 3 moles of acetone per mole of ethylenediamine and continuously charging the mixture to a continuous reactor containing a bed of a pelleted hydrogenation catalyst in the presence of at least 50% molar excess of hydrogen, based on the acetone, under reaction conditions including a temperature in the range of about 100° to about 300° C. and a pressure within the range of about 50 to about 4,000 psig, including a hydrogen partial pressure of at least about 50 to 2,500 psig at a feed rate for the mixture of ethylenediamine and acetone of about 0.5 to about 3 w/hr/v, to thereby form said N-isopropyl amine derivative of ethylenediamine,
b. said N-isopropyl secondary amine being a member selected from the group consisting of N-isopropyl secondary amine derivative and di-N,N'-secondary isopropyl derivative of ethylenediamine having the formula:

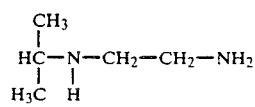

and

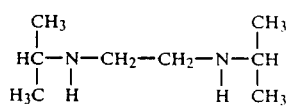

c. said hydrogenation catalyst being a pelleted nickel catalyst consisting essentially of about 60 to about 85 mole percent of nickel, about 14 to about 37 mole percent of copper and about 1 to about 5 mole percent of chromium, as chromia.

2. A method as in claim 1 wherein the reaction conditions include a temperature within the range of about 120° to about 200° C., and a pressure within the range of about 1,000 to about 4,000 psig.

3. A method as in claim 1 for preferentially preparing the N-secondary monoisopropyl derivative of ethylene diamine wherein the reaction conditions include a temperature within the range of about 130° to about 180° C., a pressure within the range of about 1,000 to about 4,000 psig, and a feed rate for the mixture of acetone and ethylenediamine within the range of about 1 to about 3 w/hr/v.

4. A method for the continuous production of the N-isopropyl secondary amine derivative of ethylenediamine and the di-N,N'-isopropyl secondary amine derivative of ethylenediamine by the reaction of acetone with ethylenediamine, characterized by a high conversion of ethylenediamine, a high selectivity to N-isopropyl ethylenediamine, and by the substantially complete inhibition of the formation of an addition product of acetone with ethylenediamine having the formula:

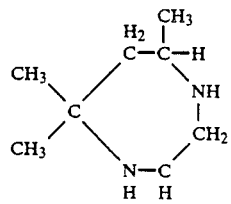

said method being further characterized by the diminished formation, during distillation, of a ternary azeotrope of ethylenediamine, N-isopropyl ethylenediamine and N,N'-di-isopropylethylenediamine and also by the diminished formation of an azeotrope of N-isopropyl ethylenediamine with piperazine, said method comprising the steps of:

a. substantially simultaneously continuously mixing ethylenediamine with acetone in the molar ratio of about 1.5 to about 1.75 moles of acetone per mole of ethylenediamine and continuously charging the mixture to a continuous reactor containing a bed of a pelleted hydrogenation catalyst in the presence of at least a 50% molar excess of hydrogen, based on the acetone, under reaction conditions including a temperature in the range of about 130° to about 180° C. and a pressure within the range of about 1,000 to about 4,000 psig, including a hydrogen partial pressure of at least about 50 to 2,500 psig at a feed rate for the mixture of ethylenediamine and acetone of about 1 to about 3 w/hr/v, to thereby form a reaction product containing a reduced amount of piperazine and also containing said N-isopropyl amine derivatives of ethylenediamine, b. separating said reaction product in distillation zone into a plurality of fractions, including a distillate fraction boiling within the range of about 137°–139° C. and consisting essentially of said N-isopropyl secondary amine derivative of ethylenediamine and a distillate fraction boiling within the range of about 167° to about 169° C. and consisting essentially of said di-N,N'-secondary isopropyl derivative of ethylenediamine, c. said hydrogenation catalyst being a pelleted nickel catalyst consisting essentially of about 60 to about 85 mole percent of nickel, about 14 to about 37 mole percent of copper and about 1 to about 5 mole percent of chromium, as chromia.

* * * * *